United States Patent [19]

Rapp et al.

[11] Patent Number: 5,543,550
[45] Date of Patent: Aug. 6, 1996

[54] PROCESS FOR THE PREPARATION OF 5-FLUOROANTHRANILIC ALKYL ESTERS AND/OR 5-FLUOROANTHRANILIC ACID

[75] Inventors: Jochen Rapp, Frankfurt; Siegfried Planker, Königstein; Theodor Papenfuhs, Frankfurt; Günter Bartels, Burgwedel, all of Germany

[73] Assignee: Hoechst Aktiengesellschaft, Germany

[21] Appl. No.: 319,306

[22] Filed: Oct. 6, 1994

[30] Foreign Application Priority Data

Oct. 8, 1993 [DE] Germany ............ 43 34 432.1

[51] Int. Cl.⁶ .............. C07C 229/52; C07C 69/76; C07C 63/04
[52] U.S. Cl. .............. 560/19; 560/47; 560/103; 562/433; 562/456; 562/458; 562/493
[58] Field of Search .............. 560/19, 47, 103; 562/456, 458, 433, 493

[56] References Cited

U.S. PATENT DOCUMENTS 4,059,627  11/1977  Kritzler et al. .............. 260/580
4,506,089  3/1985  Hackenberger et al. .............. 560/20

FOREIGN PATENT DOCUMENTS 2330669  6/1977  France .
2345788  5/1974  Germany .
2345788-A  5/1974  Germany .............. A01N 9/20

OTHER PUBLICATIONS

Journal of the American Chemical Society, The Synthesis of Some Alkyl and Dialkylaminoalkyl Esters of 2-Nitro-5-fluorobenzoic Acid and 2-Amino-fluorobenzoic Acid, Bd. 66, Jul. 1944, pp. 1165-1166.

Tetrahedron Letters, Synthesis and DNA Crosslinking Ability of a Dimeric Anthramycin Analog, Bd. 29, Nr. 40, 1988, pp. 5105-5108.

Primary Examiner—José G. Dees
Assistant Examiner—Rosalynd A. Williams
Attorney, Agent, or Firm—Connolly & Hutz

[57] ABSTRACT

The present invention relates to a process for the preparation of 5-fluoroanthranilic alkyl esters and/or 5-fluoroanthranilic acid, which comprises dissolving a 3-fluorobenzoic alkyl ester in sulfuric acid and reacting the solution with a nitrating acid at from −10° to 30° C., then adding water, separating off the nitrated reaction product and reacting it with hydrogen at from 50° to 120° C. under elevated pressure in the presence of a catalyst comprising a metal of the platinum group and sulfur, and, if desired, removing 5-fluoroanthranilic alkyl esters by distillation and hydrolyzing them to give 5-fluoroanthranilic acid.

37 Claims, No Drawings

PROCESS FOR THE PREPARATION OF 5-FLUOROANTHRANILIC ALKYL ESTERS AND/OR 5-FLUOROANTHRANILIC ACID

The present invention relates to a novel, advantageous process for the preparation of 5-fluoroanthranilic alkyl esters and/or 5-fluoroanthranilic acid.

It is known that 5-fluoroanthranilic acid can be prepared by nitrating 3-fluorobenzoic acid and then reducing the 5-fluoro-2-nitrobenzoic acid formed (Rec. Trav. Chim. Pays-Bas 1914, 33, 336, Tetrahedron Lett. 1988, 29(40), 5105–8; J. Biol. Chem. 1954, 207, 411–2).

In this synthesis, during the nitration the isomeric 3-fluoro-2-nitrobenzoic acid is also always formed, which cannot, however, be separated from 5-fluoro-2-nitrobenzoic acid. The subsequent reduction of this product mixture which contains about 2 to 3% of 3-fluoro-2-nitrobenzoic acid produces not only the desired product (5-fluoroanthranilic acid) but also, in a corresponding amount, 3-fluoroanthranilic acid which, however, cannot be separated from 5-fluoroanthranilic acid.

5-fluoroanthranilic alkyl esters can be prepared by using thionyl chloride to convert 5-fluoro-2-nitrobenzoic acid into the corresponding acid chloride, which is subsequently reacted with an alkyl alcohol to give a 5-fluoro-2-nitrobenzoic alkyl ester which in turn is converted by catalytic reduction into the corresponding 5-fluoroanthranilic alkyl ester (J. Am. Chem. Soc. 1944, 66, 1165–1166). It is known that nitrobenzoyl chlorides are thermally unstable and have a tendency to undergo decomposition reactions. For this reason they cannot be worked up by distillation and purified to the extent required. Therefore, the industrial utilization of the synthesis route appears to be highly problematical and would require a very high expenditure on safety.

DE-A 23 45 778 relates to a process for the preparation of an alkyl halonitrobenzoate, in particular methyl 5-chloro-2-nitrobenzoate, by nitration of an alkyl halobenzoate in the presence of sulfuric acid and nitric acid. In this reaction a mixture of nitric acid and sulfuric acid is used and this acid mixture is added to the reaction zone containing the alkyl halobenzoate to be reacted. The examples mentioned of an alkyl halobenzoate include methyl 5-fluoro-2-nitrobenzoate.

The implementation of the nitration, however, is only supported experimentally by a single example, namely the reaction of methyl 5-chloro-2-nitrobenzoate. Methyl 3-chlorobenzoate is dissolved in 1,2-dichloroethane, the solution is cooled to −10° C. and a mixture of nitric acid and sulfuric acid is slowly added. The yield of methyl 5-chloro-2-nitrobenzoate is 85 mol % and the purity is only 80% by weight, which represents a significant deterioration in relation to the purity of 94% by weight of the methyl 3-chlorobenzoate employed.

5-Fluoroanthranilic acid, especially isomerically pure 5-fluoroanthranilic acid, and 5-fluoroanthranilic alkyl esters are valuable precursors for the production of pharmaceuticals (Czech Patent 159 570), herbicides (U.S. Pat. No. 3,905,800, EP-B 0 109 575, U.S. Pat. No. 4,388,472), plant growth regulators (French Patent 2 541 288) and fungicides of the quinazoline type (U.S. Pat. No. 4,824,469). There is therefore a considerable interest in making these compounds industrially accessible in a simple way while observing safety requirements. Moreover, the process should ensure that the desired products are obtained not only in a high yield but also in very high purity.

This object is achieved by a process for the preparation of 5-fluoroanthranilic alkyl esters and/or 5-fluoroanthranilic acid. It comprises dissolving a 3-fluorobenzoic alkyl ester in sulfuric acid and reacting the solution with nitrating acid at from −10° to 30° C., then adding water, separating off the nitrated reaction product and reacting it with hydrogen at from 50° to 120° C. under elevated pressure in the presence of a catalyst comprising a metal of the platinum group and sulfur, and, if desired, removing 5-fluoroanthranilic alkyl esters by distillation and hydrolyzing them to give 5-fluoroanthranilic acid.

The process is based on the following equation:

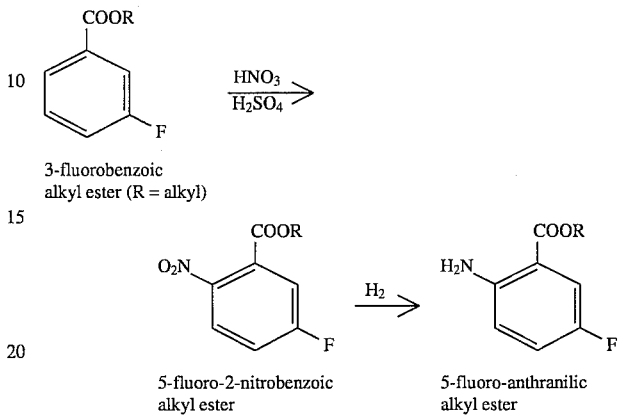

3-fluorobenzoic alkyl ester (R = alkyl)

5-fluoro-2-nitrobenzoic alkyl ester 5-fluoro-anthranilic alkyl ester

As 3-fluorobenzoic alkyl ester it is conventional to employ a $C_1$–$C_6$-alkyl ester of 3-fluorobenzoic acid.

Suitable 3-fluorobenzoic alkyl esters are methyl 3-fluorobenzoate, ethyl 3-fluorobenzoate, n-propyl 3-fluorobenzoate, isopropyl 3-fluorobenzoate, n-butyl 3-fluorobenzoate and/or isobutyl 3-fluorobenzoate.

Highly suitable starting materials are methyl 3-fluorobenzoate and/or ethyl 3-fluorobenzoate.

In a range of cases it may be advantageous to use methyl 3-fluorobenzoate as the 3-fluorobenzoic alkyl ester. The 3-fluorobenzoic alkyl ester is dissolved in sulfuric acid, and in this context care should be taken that the temperatures selected during the dissolution are not too high. The 3-fluorobenzoic alkyl ester is generally dissolved at from 0° to 20° C. in sulfuric acid. However, it is possible to carry out the dissolution at higher temperatures, for example up to 40° C.

The sulfuric acid used for the dissolution should as far as possible contain no water, so should rather be used in concentrated form. Commonly the 3-fluorobenzoic alkyl ester is dissolved in from 98 to 100% strength by weight $H_2SO_4$.

When carrying out the process according to the invention care should be taken that the sulfuric acid is employed in a sufficient quantity. It is generally sufficient to dissolve the 3-fluorobenzoic alkyl ester in from 2 to 10 parts, in particular from 3 to 6 parts, by weight of $H_2SO_4$, based on 3-fluorobenzoic alkyl ester.

The 3-fluorobenzoic alkyl ester dissolved in sulfuric acid is then treated with nitrating acid. The term nitrating acid refers to a mixture of $HNO_3$ and $H_2SO_4$, both the nitric acid and the sulfuric acid being used in a highly concentrated form, i.e. with a water content of from 0 to 3% by weight.

The nitrating acid usually employed is a mixture of from 95 to 100% by weight strength $HNO_3$ and from 98 to 100% by weight strength $H_2SO_4$. The mixture generally used as nitrating acid comprises one part by weight of $HNO_3$ and from 2 to 6 parts by weight of $H_2SO_4$.

The nitration of the 3-fluorobenzoic alkyl ester can be carried out either with an excess or with a deficit of nitrating acid. Conventionally, from 0.8 to 1.2 equivalents of nitrating acid (based on the nitric acid it contains) are employed per mole of 3-fluorobenzoic alkyl ester. In a series of cases it may be advantageous to employ from 0.95 to 1.05 equivalents of nitrating acid (based on the nitric acid it contains)

per mole of 3-fluorobenzoic alkyl ester. The reaction is particularly simple if the nitrating acid is added in an equivalent quantity based on 3-fluorobenzoic alkyl ester.

During the reaction with nitrating acid, excessive temperatures should be avoided. It is generally sufficient to carry out the nitration at from −10° to +30° C. For a series of cases a temperature range from 0° to 30° C., in particular from 0° to 20° C., proves to be sufficient.

When the nitration is over water is added to the reaction mixture obtained. During the dilution with water the temperature should not rise to too high a level. It is recommended, if desired, to cool the reaction mixture and/or the added water. The addition of water should generally be carried out such that a temperature range of from about 40° to about 60° C. is observed.

Advantageously, the reaction mixture obtained after the nitration is diluted with water until the 5-fluoro- 2-nitrobenzoic alkyl ester, still containing minor quantities of 3-fluoro-2-nitrobenzoic alkyl ester, is deposited. The process is particularly simple if, in this context, a temperature is chosen at which the nitro ester can be separated off in liquid form. The organic phase containing the desired product is separated from the aqueous phase containing sulfuric acid. The aqueous phase can be regenerated to give reusable 100% strength sulfuric acid, by means of methods which are common in industry. The organic phase, if desired after washing with water at from 40° to 60° C., is employed in the subsequent reduction.

It is to be regarded as surprising that the nitration alone provides a valuable product in high purity. In addition to the desired 5-fluoro-2-nitrobenzoic alkyl ester no more than about 2% by weight or less of the unwanted 3-fluoro-2-nitrobenzoic alkyl ester is found. This might be regarded as an unexpected result in view of the nitration of methyl 3-chlorobenzoate, which is supported experimentally in DE-A 23 45 788 and leads to a considerable reduction in the purity of the valuable product. In this connection, however, it should be pointed out that a proportion of about 2% by weight of 3-fluoro-2-nitrobenzoic alkyl ester represents an order of magnitude which is not tolerable for the subsequent use of 5-fluoro-2-benzoic alkyl ester.

A principal advantage of the process according to the invention is that it can be used flexibly without having to accept a deterioration in the purity of 5-fluoroanthranilic ester and/or 5-fluoroanthranilic acid. Indeed, it opens up the possibility, as desired or required, either of employing the reaction mixture obtained after nitration for the reduction, without an additional purification, or alternatively of almost completely separating off, in a comparatively simple manner, the unwanted 3-fluoro-2-nitrobenzoic alkyl ester and of passing the resulting isomer-free 5-fluoro- 2-nitrobenzoic alkyl ester to the reduction. In addition to this, the possibility exists of converting the isomer-free 5-fluoro-2-nitrobenzoic alkyl ester by hydrolysis into isomer-free 5-fluoro-2-nitrobenzoic acid and then reducing the latter. Reduction of the isomer-free nitration product yields alternatively an isomer-free 5-fluoroanthranilic alkyl ester or isomer-free 5-fluoroanthranilic acid. If desired, mixtures of these two compounds can also be prepared.

The purification of the reaction mixture contaminated with 3-fluoro-2-nitrobenzoic alkyl ester is carried out at comparably low expense by melt crystallization. In the melt crystallization the nitration product, which is present in liquid form, is induced to crystallize completely by cooling and is then heated, very slowly at a rate of from 0.5° to 2° C. per hour, until liquid fractions are formed which can be separated off from the solid (residual regulus) using appropriate apparatus (dropping-type apparatus, crystallization columns). The liquid fractions preferably contain the 3-fluoro-2-nitrobenzoic alkyl ester while the desired product (5-fluoro-2-nitrobenzoic alkyl ester) remains in the residual regulus. The purification operation is monitored by analyzing the melted fractions. As soon as the melted fraction gives evidence of isomerically pure 5-fluoro-2-nitrobenzoic alkyl ester, the purification is complete and the residual regulus is liquefied by forced melting and passed on for further processing. The fractions obtained beforehand ("drop oils") can be passed, in whole or in part, to a downstream melt crystallization.

The hydrolysis of the 5-fluoro-2-nitrobenzoic alkyl ester, which is obtained in isomerically pure form in this way, can be carried out either in an alkaline or in an acid medium. Acidic hydrolysis using, for example, an aqueous mineral acid is generally preferred.

For further processing the nitrated reaction product, as mentioned previously, is reacted with hydrogen in the presence of a catalyst comprising a metal of the platinum group and sulfur. Conventionally from 0.01 to 0.1% by weight of the platinum group metal is employed, based on nitrated reaction product.

Suitable catalysts are those containing Pd or Pt and sulfur. The reduction is particularly simple if supported catalysts, especially supported catalysts containing Pd or Pt, are employed. Highly suitable catalysts are those containing Pd or Pt on active charcoal as support with minor amounts of a sulfur compound. The sulfur compound can be added separately to the catalyst or may alternatively be present in the catalyst and may be used, for example, in the form of a sulfited or sulfided catalyst, if desired in the presence of a further sulfur compound. The catalyst contains minor amounts of the sulfur compound. It is usual to employ sulfur compound and platinum metal in a ratio of (from 0.05 to 40):1, in particular (from 0.2 to 10):1. Suitable sulfur compounds are thiourea, dimethyl sulfoxide, thiophene and/or an alkali metal sulfite.

It is recommended to carry out the reaction of the nitrated reaction product with hydrogen in the presence of an inert solvent. Suitable inert solvents which can be used are $H_2O$, an alcohol, especially an aliphatic alcohol having 1 to 5 carbon atoms, toluene, xylene, mixtures of isomeric xylenes, chlorobenzene and/or dichlorobenzene.

If the intention is to react an isomerically pure 5-fluoro-2-nitrobenzoic acid with hydrogen, then it is advantageous to use an aqueous solution of a salt of this isomerically pure 5-fluoro-2-nitrobenzoic acid as the nitrated reaction product.

The reaction with hydrogen is carried out under pressure, a pressure of from 0.5 to 10 and in particular from 1.0 to 3.0 MPa being sufficient. As mentioned previously, the reduction with hydrogen is carried out at from 50° to 120° C. In many cases it has proven sufficient to carry out this reaction at from 60° to 100° C. When the reduction is complete the catalyst is removed by filtration and the product, dissolved in the solvent, is separated from the aqueous phase formed. The organic phase is freed of solvent by distillation to give the 5-fluoroanthranilic alkyl ester as the bottom product which, if required, is purified by distillation. If an isomer-containing nitro ester is employed in the reduction, the 5-fluoroanthranilic alkyl ester, which contains 3-fluoroanthranilic ester as a by-product, can be purified by fractional distillation, separating off 3-fluoroanthranilic alkyl ester as the initial fraction and then leaving 5-fluoroanthranilic alkyl ester as the bottom product or obtaining it, after further distillation, as isomerically pure product. If desired the isomerically pure 5-fluoroanthranilic alkyl ester can be converted by hydrolysis into 5-fluoroanthranilic acid. It is therefore not absolutely necessary to purify the crude, nitrated reaction product in order to obtain an isomerically pure 5-fluoroanthranilic alkyl ester and/or isomerically pure 5-fluoroanthranilic acid. The appropriate purification step can also be carried out at a later point in time, namely after the end of the reduction. The process according to the invention therefore proves to be variable in a particularly advantageous way and can be adapted correspondingly to the requirements of each particular case. Indeed, it not only produces, on the one hand, isomerically pure 5-fluoroanthranilic alkyl ester and, on the other hand, isomerically pure 5-fluoroanthranilic acid but also, as required, isomerically pure 5-fluoro-2-nitrobenzoic alkyl ester and isomerically pure 5-fluoro-2-nitrobenzoic acid, and mixtures of these compounds.

The examples which follow illustrate the invention without limiting it.

EXPERIMENTAL SECTION

EXAMPLE 1

504 parts of ethyl 3-fluorobenzoate (purity 99.7% by weight) are dissolved in 2025 parts of 100% strength sulfuric acid, with stirring and gentle cooling, at not more than 35° C. A mixture of 210 parts of 98% strength nitric acid and 420 parts of 100% strength sulfuric acid is then added dropwise over 90 minutes at 10°–20° C. and the mixture is subsequently stirred without cooling for one hour. Then the nitrating mixture is run in to 995 parts of ice-water at a rate such that a temperature of 50° C. is not exceeded, and the ethyl fluoronitrobenzoate which separates out as a liquid is isolated and washed in three portions until neutral with 200 parts of hot water at 50° C.

For reduction, the product can be employed in moist form after determining the water content (cf. Example 5), and for isomer separation by melt crystallization (cf. Example 3) it is dried in vacuo at 100° C. 580 parts of ethyl fluoronitrobenzoate are obtained, comprising 98.2% ethyl 5-fluoro-2-nitrobenzoate and 1.8% ethyl 3-fluoro- 2-nitrobenzoate, with a solidification point s.p. of 44.6° C. and a purity (GC) of >99%, based on isomer mixture. This corresponds to a yield of 90% of theory based on the ethyl 3-fluorobenzoate employed.

EXAMPLE 2

72.4 parts of methyl 3-fluorobenzoate are dissolved in 300 parts of 100% strength sulfuric acid with stirring at not more than 30° C., the solution is cooled to 0°–10° C. and then, over the course of 2 hours, a mixture of 32.7 parts of 98% strength nitric acid and 78.3 parts of 100% strength sulfuric acid is added dropwise with continuous cooling at 0°–10° C., and the mixture is stirred without cooling for 3 hours, during which the temperature of the nitrating mixture rises to 20° C. Then 175 parts of water are added dropwise, again with continuous cooling. The methyl fluoronitrobenzoate separates out as an oil which is separated off, washed until neutral in portions with 350 parts of water, and dried in vacuo at 100° C. 92 parts of methyl fluoronitrobenzoate are obtained, comprising 98.1% methyl 5-fluoro-2-nitrobenzoate and 1.9% methyl 3-fluoro-2-nitrobenzoate, with an s.p. of 34.0° C. and a purity (GC) of >99% based on isomer mixture. This corresponds to a yield of 98.4% of theory based on the methyl 3-fluorobenzoate employed.

EXAMPLE 3

1295.8 parts of the dry ethyl fluoronitrobenzoate prepared in accordance with Example 1 (isomer mixture of 98.2%= 1272.5 parts of ethyl 5-fluoro-2-nitrobenzoate and 1.8%= 23.3 parts of ethyl 3-fluoro-2-nitrobenzoate) of s.p. 44.6° C. are placed, in liquid melt form, into a dropping apparatus (a heated vertical glass tube with a bottom outlet which can be closed off, diameter 5 cm, height 60 cm) and induced to crystallize completely overnight by cooling to 20° C. The next morning the dropping apparatus is heated continuously at a rate of 1° C./hour with the bottom outlet opened, and the fractions which drop down are analyzed by gas chromatography for the instantaneous isomeric composition (fraction analysis in the table below).

At 34° C. melted product enriched in ethyl 3-fluoro-2-nitrobenzoate begins to drop down. When a temperature of 44.5° C. is reached about 25% of the initial product has dropped down, containing 98% of the unwanted isomer. The residual regulus remaining in the dropping apparatus is isomerically pure ethyl 5-fluoro-2-nitrobenzoate with a purity of 99.95% (GC), s.p. 45.6° C.

| Fraction | Temp. (°C.) | Quantity (g) | Ethyl 3-fluoro-2-nitrobenzoate | | | % of initial product (cumulative) |
| --- | --- | --- | --- | --- | --- | --- |
| | | | Content (%) | Quantity (g) | Σ Quantity (g) | |
| 1 | 34–36 | 18.3 | 31.1 | 5.7 | 5.7 | 1.4 |
| 2 | 36–38 | 17.3 | 18.5 | 3.2 | 8.9 | 2.7 |
| 3 | 38–40 | 36.1 | 14.4 | 5.2 | 14.1 | 5.5 |
| 4 | 40–42 | 8.9 | 9.0 | 0.8 | 14.9 | 6.2 |
| 5 | 42–43 | 14.1 | 6.4 | 0.9 | 15.8 | 7.3 |
| 6 | 43–43.5 | 42.4 | 4.5 | 1.9 | 17.7 | 10.6 |
| 7 | 43.5 | 27.6 | 4.0 | 1.1 | 18.8 | 12.7 |
| 8 | 43.5 | 42.5 | 4.0 | 1.7 | 20.5 | 16.0 |
| 9 | 43.5–44 | 68.4 | 2.3 | 1.6 | 22.1 | 21.3 |
| 10 | 44–44.5 | 43.9 | 1.8 | 0.8 | 22.9 | 24.7 |

The yield of isomerically pure ethyl 5-fluoro-2-nitrobenzoate is consequently 75.3% based on isomer mixture employed. By returning fractions 4–10 to the subsequent melt crystallization the yield of pure ester can be increased to 89–91%.

EXAMPLE 4

912 parts of 20% strength hydrochloric acid and 600 parts of glacial acetic acid are added to 213 parts of isomerically pure ethyl 5-fluoro-2-nitrobenzoate prepared by melt crystallization in accordance with Example 3, and the mixture is then heated at 100° C. for 20 hours, 545 parts of aqueous ethanol being distilled off in the course of the hydrolysis.

The mixture is then cooled to room temperature and the 5-fluoro-2-nitrobenzoic acid which precipitates out is isolated on a suction filter. The filter cake is washed until neutral with 300–400 parts of water. The mother filtrate is concentrated to about 150 parts. As is it cooled, further 5-fluoro- 2-nitrobenzoic acid is precipitated which, after filtration and washing, is purified with the initial precipitate.

230 parts of moist product (water content 21.3%) are obtained which can be used as it is for reduction (cf. Example 7).

By drying at 100° C. in vacuo, 181 parts of isomerically pure 5-fluoro-2-nitrobenzoic acid are obtained with a melting point of 134°–135° C., corresponding to a yield of 97.8% of theory.

EXAMPLE 5

344 parts of xylene, one part of triethylamine, 4.5 parts of catalyst (5% Pt on charcoal, moist, water content 50%) and 0.05 part of sodium sulfite are placed in a hydrogenation autoclave. After flushing the gas space with nitrogen and hydrogen three times each, the autoclave is heated to 80°–85° C. with stirring and, at a hydrogen pressure of 1.5–2.0 MPa, a solution of 400 parts of ethyl 5-fluoronitrobenzoate (isomer mixture prepared in accordance with Example 1, comprising 98.2%=392.8 parts of ethyl 5-fluoro-2-nitrobenzoate and 1.8%=7.2 parts of ethyl 3-fluoro-2-nitrobenzoate) in 516 parts of xylene to which 1 part of triethylamine has also been added is pumped in over the course of 90 minutes.

When there is no further drop in pressure, stirring is continued for 20 minutes at 85°–90° C., the autoclave is let down, and the catalyst is filtered on a pressure filter at 30°–60° C.

The aqueous phase is separated off from the filtrate, the xylene is distilled and the remaining, crude ethyl fluoroanthranilate is fractionated in vacuo at 1 torr. After a 5% initial fraction (based on crude product employed), containing all of the isomeric ethyl 3-fluoroanthranilate (b.p.$_1$: 85°–95° C.), pure ethyl 5-fluoroanthranilate distils over (b.p.$_1$: 102° C.). It is obtained in a yield of 93.5% of theory, based on the isomer mixture employed. The purity (GC) is 99.9%.

If the 0.05 part of sodium sulfite is replaced by 0.01 part of thiourea and the triethylamine by aliquot quantities of morpholine, then the result is identical for the same procedure.

EXAMPLE 6

In accordance with Example 5, 316 parts of methanol, 1.5 parts of triethylamine and 5 parts of catalyst (5% Pt on charcoal, moist, water content 50%) and 0.05 part of dimethyl sulfoxide are initially charged and, at a hydrogen pressure of 1.0 to 1.5 MPa at 85°–90° C., a solution of 348 parts of methyl 5-fluoronitrobenzoate (isomer mixture prepared in accordance with Example 2 comprising 98.1%= 341.4 parts of methyl 5-fluoro-2-nitrobenzoate and 1.9%= 6.6 parts of methyl 3-fluoro-2-nitrobenzoate) in 395 parts of methanol, to which 0.5 part of triethylamine has also been added, is pumped in over the course of 60 minutes. After the end of the reaction the catalyst is separated off by filtration and the filtrate is fractionally distilled. After an initial fraction (methanol/water), at 90°–103° C./1 torr an intermediate fraction is obtained which contains all of the methyl 3-fluoroanthranilate (17.7 parts=6%), after which isomerically pure methyl 5-fluoroanthranilate (b.p.$_1$: 104° C.) distills over. 272 parts are obtained with a purity of 99.9%, corresponding to a yield of 92% of theory based on the isomer mixture employed.

EXAMPLE 7

In accordance with Example 5, 400 parts of isomerically pure ethyl 5-fluoro-2-nitrobenzoate prepared by melt crystallization in accordance with Example 3 are catalytically reduced.

After separating off the catalyst and the aqueous phase and drying the organic phase in vacuo at 100 torr and at 100° C., the isomerically pure ethyl 5-fluoroanthranilate is obtained with a purity (GC) of 99.7% in a yield of 98.9%.

If the isomerically pure ethyl 5-fluoro-2-nitrobenzoate is replaced by aliquot parts of a correspondingly prepared, isomerically pure n-propyl 5-fluoro-2-nitrobenzoate, and the same procedure is employed, then the isomerically pure n-propyl 5-fluoroanthranilate is obtained in comparable yield and quality.

EXAMPLE 8

450 parts of water and 2.5 parts of catalyst (5% Pt on charcoal, sulfited, moist, water content 50%) are placed in a hydrogenation autoclave. After flushing the gas space with nitrogen and hydrogen three times each, the autoclave is heated to 90° C. with stirring, and, at a hydrogen pressure of 1.0–2.0 MPa, a solution of 231 parts of isomerically pure 5-fluoro-2-nitrobenzoic acid (prepared by acidic hydrolysis of melt-crystallized ethyl 5-fluoro-2-nitrobenzoate in accordance with Examples 3+4) in 400 parts of 12.5% strength sodium hydroxide is pumped in over the course of 60 minutes.

When there is no further drop in pressure, stirring is continued for 20 minutes at 90° C., the autoclave is let down, the catalyst is filtered off at 40°–60° C. and the aqueous filtrate is acidified with hydrochloric acid. The isomerically pure 5-fluoroanthranilic acid precipitates out. It is filtered off, washed until neutral with water and dried in vacuo at 100° C.

179 parts of isomerically pure 5-fluoroanthranilic acid with a melting point of 182°–182.5° C. and a purity of 99.7% (HPLC) are obtained, corresponding to a yield of 92.4% of theory based on the isomerically pure 5-fluoro-2-nitrobenzoic acid employed.

EXAMPLE 9

183 parts of isomerically pure ethyl 5-fluoroanthranilate, prepared in accordance with Example 5, and 912 parts of 20% strength hydrochloric acid are heated under reflux for 10 hours. The ethanol formed and the majority of the aqueous hydrochloric acid are then removed by distillation. The remaining product is adjusted to a pH of 4.0 using sodium hydroxide solution. The isomerically pure 5-fluoroanthranilic acid which crystallizes out is filtered off, washed until neutral with water and dried in vacuo at 100° C.

149 parts of isomerically pure 5-fluoroanthranilic acid with a melting point of 182°–182.5° C. and a purity of 99.8% (HPLC) are obtained, corresponding to a yield of 96.1% of theory based on the isomerically pure ethyl 5-fluoroanthranilate employed.

COMPARISON EXAMPLE 1

(Nitration of methyl 3-fluorobenzoate in accordance with DE-A 23 45 788, Example 1)

A mixture of 33.8 parts of 95% strength nitric acid and 81.6 parts of 98.6% strength sulfuric acid is added dropwise to an initially charged solution of 172.4 parts of methyl 3-fluorobenzoate (purity 99.8%) in 50 parts of methylene chloride over 3 hours at −10° C. The mixture is then stirred for 2 hours at −10° C. and for 3 hours at 0°–30° C. Subsequently the methyl fluoronitrobenzoate is extracted from the reaction mixture using 1,2-dichloroethane and is isolated by evaporating the solvent.

79.8 parts of product are obtained, having the following composition:

13.3%=10.6 parts of methyl 3-fluorobenzoate 84.4%=67.4 parts of methyl 5-fluoro-2-nitrobenzoate 2.3%=1.8 parts of methyl 3-fluoro-2-nitrobenzoate;

in other words, the methyl 5-fluoro-2-nitrobenzoate desired is formed in 85.3% yield. Its purity is only 84.4%, and the isomer ratio, at 2.7% methyl 3-fluoro- 2-nitrobenzoate to 97.3% methyl 5-fluoro-2-nitrobenzoate, is poorer than with the process according to the invention (1.8–1.9% methyl 3-fluoro-2-nitrobenzoate to 98.1–98.2% methyl 5-fluoro-2-nitrobenzoate).

COMPARISON EXAMPLE 2

Catalytic reduction of ethyl 5-fluoronitrobenzoate (isomer mixture prepared as in Example 1) in the absence of moderators (sulfur compounds)

Following the procedure of Example 5 but omitting the addition of 0.05 part of sodium sulfite or 0.01 part of thiourea, after catalytic reduction and distillative workup ethyl 5-fluoroanthranilate is obtained in a comparable yield but, because it contains 0.3–0.4% ethyl anthranilate (as a result of hydrogenolytic elimination of fluorine), it cannot be employed for subsequent reactions. Distillative removal of this impurity is not possible even with intense fractionation, since it has the same boiling point as methyl 5-fluoroanthranilate.

We claim:

1. A process for the preparation of a 5-fluoroanthranilic alkyl ester, 5-fluoroanthranilic acid, or a mixture thereof, which comprises:

dissolving a 3-fluorobenzoic alkyl ester in a medium consisting essentially of essentially solvent-free sulfuric acid and reacting the resulting solution with nitrating acid at from −10° to 30° C., then adding water, separating off the nitrated reaction product and optionally including the step of hydrolyzing said nitrated reaction product to form the corresponding nitrated fluorobenzoic acid, reacting said nitrated reaction product or the corresponding nitrated fluorobenzoic acid with hydrogen at from 50° to 120° C. under elevated pressure in the presence of a catalyst comprising a metal of the platinum group and sulfur, and recovering a 5-fluoroanthranilic alkyl ester or 5-fluoroanthranilic acid or a mixture thereof as the product.

2. The process as claimed in claim 1, wherein the 3-fluorobenzoic alkyl ester comprises a $C_1$–$C_6$-alkyl 3-fluorobenzoate.

3. The process as claimed in claim 2, wherein the 3-fluorobenzoic alkyl ester is methyl 3-fluorobenzoate, ethyl 3-fluorobenzoate, n-propyl 3-fluorobenzoate, isopropyl 3-fluorobenzoate, n-butyl 3-fluorobenzoate, isobutyl 3-fluorobenzoate or a mixture thereof.

4. The process as claimed in claim 2, wherein the 3-fluorobenzoic alkyl ester is methyl 3-fluorobenzoate, ethyl 3-fluorobenzoate or a mixture thereof.

5. The process as claimed in claim 2, wherein the 3-fluorobenzoic alkyl ester is methyl 3-fluorobenzoate.

6. The process as claimed in claim 1, wherein the 3-fluorobenzoic alkyl ester is dissolved in $H_2SO_4$ at from 0° to 20° C.

7. The process as claimed in claim 1, wherein the 3-fluorobenzoic alkyl ester is dissolved in from 98 to 100% strength by weight $H_2SO_4$.

8. The process as claimed in claim 1, wherein the 3-fluorobenzoic alkyl ester is dissolved in concentrated $H_2SO_4$.

9. The process as claimed in claim 1, wherein the 3-fluorobenzoic alkyl ester is dissolved in from 2 to 10 parts by weight of $H_2SO_4$, based on 3-fluorobenzoic alkyl ester.

10. The process as claimed in claim 1, wherein the nitrating acid employed is a mixture of from 95 to 100% strength by weight of $HNO_3$ and from 98 to 100% by weight of $H_2SO_4$.

11. The process as claimed in claim 1, wherein the nitrating acid employed is a mixture of 1 part by weight $HNO_3$ and from 2 to 6 parts by weight of concentrated $H_2SO_4$.

12. The process as claimed in claim 1, wherein from 0.8 to 1.2 equivalents of nitrating acid (based on the nitric acid it contains) are employed per mole of 3-fluorobenzoic alkyl ester.

13. The process as claimed in claim 1, wherein from 0.95 to 1.05 equivalents of nitrating acid (based on the nitric acid it contains) are employed per mole of 3-fluorobenzoic alkyl ester.

14. The process as claimed in claim 1, wherein the 3-fluorobenzoic alkyl ester is reacted with nitrating acid at from 0° to 20° C.

15. The process as claimed in claim 1, wherein after nitration the reaction mixture is diluted with water at from 40° to 60° C.

16. The process as claimed in claim 1, wherein the nitrated reaction product consists essentially of 5-fluoro-2-nitrobenzoic alkyl ester and no more than about 2% by weight of 3-fluoro-2-nitrobenzoic alkyl ester and is separated off by phase separation and is optionally washed with hot water at from 40° to 60° C.

17. The process as claimed in claim 1, wherein the nitrated reaction product comprises 5-fluoro-2-nitrobenzoic acid alkyl ester and 3-fluoro-2-nitrobenzoic alkyl ester and the 3-fluoro-2-nitrobenzoic alkyl ester is separated off from the nitrated reaction product by melt crystallization and the 5-fluoro-2-nitrobenzoic alkyl ester which remains is optionally converted into 5-fluoro-2-nitrobenzoic acid by hydrolysis.

18. The process as claimed in claim 1, wherein the nitrated reaction product is reacted with hydrogen in the presence of from 0.01 to 0.1% by weight of a platinum group metal, based on nitrated reaction product.

19. The process as claimed in claim 1, wherein the nitrated reaction product is reacted with hydrogen in the presence of a catalyst containing Pd or Pt and sulfur or a sulfur compound.

20. The process as claimed in claim 1, wherein the catalyst employed comprises Pd or Pt on active charcoal with minor amounts of a sulfur compound.

21. The process as claimed in claim 1,
wherein the catalyst employed comprises sulfited or sulfided Pd or Pt on active charcoal with minor amounts of a sulfur compound.

22. The process as claimed in claim 19,
wherein the catalyst contains sulfur compound and platinum metal in a ratio of from 0.05:1 to 40:1.

23. The process as claimed in claim 19,
wherein the sulfur compound employed is thiourea, dimethyl sulfoxide, thiophene and/or an alkali metal sulfite.

24. The process as claimed in claim 1,
wherein the nitrated reaction product is reacted with hydrogen in the presence of an inert solvent.

25. The process as claimed in claim 24,
wherein the inert solvent employed is $H_2O$, an alcohol, toluene, xylene, chlorobenzene and/or dichlorobenzene.

26. The process as claimed in claim 1,
wherein 5-fluoro-2-nitrobenzoic acid alkyl ester is recovered from the nitrated reaction product and is hydrolyzed to a salt of 5-fluoro-2-nitrobenzoic acid, which salt is essentially isometrically pure.

27. The process as claimed in claim 1,
wherein said elevated pressure during the reaction with hydrogen ranges from 0.5 to 10 MPa.

28. The process as claimed in claim 1,
wherein the reaction with hydrogen is carried out at from 60° to 100° C.

29. The process as claimed in claim 1, which comprises:
separating off said nitrated reaction product,
reacting said nitrated reaction product with hydrogen,
recovering a 5-fluoroanthranilic alkyl ester product, and optionally hydrolyzing said alkyl ester product to 5-fluoroanthranilic acid.

30. A process for the preparation of a 5-fluoro-2-nitrobenzoic alkyl ester, which process comprises:
dissolving a 3-fluorobenzoic alkyl ester in a medium consisting essentially of essentially solvent-free sulfuric acid and reacting the resulting solution with nitrating acid at from −10° to 30° C., then adding water, and
separating off the nitrated reaction product, which consists essentially of 5-fluoro-2-nitrobenzoic alkyl ester and no more than about 2% by weight of 3-fluoro-2-nitrobenzoic alkyl ester.

31. The process as claimed in claim 30, wherein the 3-fluorobenzoic alkyl ester is a $C_1$–$C_6$-alkyl 3-fluorobenzoate.

32. The process as claimed in claim 30, wherein the 3-fluorobenzoic alkyl ester is dissolved in $H_2SO_4$ at from 0° to 20° C.

33. The process as claimed in claim 30, wherein the essentially solvent-free sulfuric acid is 98 to 100% by weight $H_2SO_4$.

34. The process as claimed in claim 30, wherein the 3-fluorobenzoic alkyl ester is dissolved in from 2 to 10 parts by weight of $H_2SO_4$, based on 3-fluorobenzoic alkyl ester.

35. The process as claimed in claim 30, wherein the nitrating acid comprises a mixture of 1 part by weight $HNO_3$ and from 2 to 6 parts by weight of concentrated $H_2SO_4$.

36. The process as claimed in claim 30, wherein, after said reacting of the resulting solution with nitrating acid, the reaction mixture is diluted with water at from 40° to 60° C.

37. The process as claimed in claim 30, wherein the 3-fluoro- 2-nitrobenzoic alkyl ester is separated off from the nitrated reaction product by melt crystallization and the 5-fluoro-2-nitrobenzoic alkyl ester which remains is optionally converted into 5-fluoro-2-nitrobenzoic acid by hydrolysis.

\* \* \* \* \*